United States Patent [19]

McGee et al.

[11] Patent Number: 4,987,250

[45] Date of Patent: Jan. 22, 1991

[54] SYNTHESIS OF HYDROXY SULFONIC ACIDS

[75] Inventors: Dennis E. McGee, LaVerne; Ted S. Hallen, Placentia, both of Calif.

[73] Assignee: Union Oil Company of California, Los Angeles, Calif.

[21] Appl. No.: 299,728

[22] Filed: Jan. 19, 1989

Related U.S. Application Data

[62] Division of Ser. No. 101,146, Sep. 25, 1987, Pat. No. 4,910,330.

[51] Int. Cl.$^5$ ............................................. C07C 303/00
[52] U.S. Cl. ..................................... 562/118; 562/108; 562/110; 562/111; 562/41
[58] Field of Search ................. 562/118, 41, 110, 111, 562/108

[56] References Cited

U.S. PATENT DOCUMENTS 4,239,696  12/1980  Schreyer et al. .................... 562/118
4,910,330   3/1990  McGee et al. ...................... 560/222

OTHER PUBLICATIONS

Chem Abst Sjoberg (1939), p. 2106(8).
Gilbert Sulfonation & Related Reactors (1965), p. 220.

*Primary Examiner*—Alan Siegel
*Attorney, Agent, or Firm*—Gregory F. Wirzbicki; Arthur E. Oaks; Michael A. Kondzella

[57] ABSTRACT

Hydroxy sulfonic acids in general and isethionic acid (2-hydroxy ethyl sulfonic acid) in particular can be prepared at 99+% purity and good yields by the selective oxidation of a precursor hydroxy mercaptan with hydrogen peroxide. The resulting product is pure enough to be used directly in the synthesis of sulfo-acrylic esters which are finding considerable use as stabilizers in producing vinylidene chloride copolymers used for FDA approved packaging films.

22 Claims, 1 Drawing Sheet

SYNTHESIS OF HYDROXY SULFONIC ACIDS

This application is a division, of application Ser. No. 101,146, filed Sept. 25, 1987 now U.S. Pat. No. 4,910,330.

FIELD OF THE INVENTION

This invention relates generally to a process for the preparation of organic sulfonic acids, and particularly to the preparation of organic hydroxy sulfonic acids, and most particularly to the preparation of isethionic acid and olefinically unsaturated carboxylic acid esters thereof.

BACKGROUND OF THE INVENTION

Hydroxy sulfonic acids and, more particularly, 2-hydroxyethane sulfonic acid, more commonly known as isethionic acid (ITA), have been prepared by a variety of methods over the past century. For example, the Tenth Edition of the *Merck Index*, at page 4960, describes ITA synthesis procedures in which ethylene is treated with a sulfonating agent such as chlorosulfonic acid and ethylene oxide with sulfur trioxide. Such methods, however, yield a product contaminated with salts such as chlorides and sulfates. Such contaminated products are undesired in a number of applications where the salt-free acid, having an amount of contaminating salts below about 0.1% is required or desired. One such application is the formation of sulfo esters, such as sulfo ethyl and sulfo propyl methacrylate, which find wide use as stabilizers in vinylidene chloride copolymers used for packaging films. Since the prior art methods are found to produce sulfonic acid compositions containing high, and usually undesirable, levels of contaminants, methods such as ion exchange chromatography have been used either to remove these impurities or to convert alkali metal isethionates, disclosed for example in U.S. Pat. No. 2,899,461 to Smith, to the acid form. However, such methods are expensive and difficult to carry out.

As a result, a number of other approaches to producing low impurity alkyl sulfonic acids have been investigated. For example, Koenig in U.S. Pat. No. 2,892,852 describes a process for producing such acids by the oxidation of organic thioethers or thioacetic acid esters with peracetic acid in acetic acid. Other processes use potassium permanganate, nitric acid or ozone as the oxidizing agent, see Asinger, *Journal Praktische Chemie*, (4)(2), Vol. 2, pp. 241–242 (1955). However, in all the above-cited processes, the yields achieved have proven to be only moderate and these processes have found only slight use for industrial purposes. This is also true of a process involving the electrolytic oxidation of methyl mercaptan as disclosed in U.S. Pat. No. 2,727,920. There is also described in that patent the reaction of mercaptans with nitric acid, which, however, cannot be employed for large-scale processes because of the explosive-like acceleration of the reaction velocity.

It is additionally known that hydrogen peroxide can oxidize certain mercaptans provided that a sufficient amount of carboxylic acid is also present. Consequently, it was thought that the percarboxylic acid formed from the carboxylic acid and the hydrogen peroxide was the true active agent (Showell, *Journal of Organic Chemistry*, Vol. 27, (1962), pp. 2853–2858). It is particularly disadvantageous in this process that it results in a product which is a mixture of alkyl sulfonic acids and carboxylic acids or percarboxylic acids from which the desired alkyl sulfonic acid is recovered in pure form only with difficulty. In the particular case of isethionic acid synthesis, techniques such as solvent extraction or distillation, which are often used to remove such compounds, are not feasible because of the solubilities and physical characteristics of isethionic acid.

Most recently, Schreyer et al. in U.S. Pat. No. 4,239,696 has disclosed a process in which alkyl sulfonic acids are prepared by the oxidation of a stoichiometric excess of an alkyl mercaptan or dialkyl disulfide, dissolved or suspended in an alkyl sulfonic acid, with hydrogen peroxide, and in the absence of percarboxylic acids. In the disclosed process, a 1 to 35 mole percent of alkyl sulfonic acid, based on the alkyl mercaptan or dialkyl disulfide used, is preferably employed. Schreyer further discloses that since no carboxylic acids are involved in this synthesis, many of the aforementioned purification problems are avoided.

BRIEF DESCRIPTION OF THE INVENTION

The process of the present invention relates to the preparation of sulfonic acids by the reaction of hydroxy mercaptans with hydrogen peroxide. In a particular aspect of the invention, the process involves preparing hydroxy sulfonic acids at relatively low cost, with high yields and at extremely high purity. One major achievement of the invention is that hydroxy sulfonic acids in general, and isethionic acid in particular, can be produced having a level of purity and a concentration such that the product of said process can, as produced, be reacted with an olefinically unsaturated carboxylic acid to produce polymerizable sulfo esters.

In its broadest aspect, the invention involves the oxidation of hydroxy mercaptans with hydrogen peroxide to form sulfonic acids, and the reaction does not require the presence of other acids such as carboxylic, percarboxylic or sulfonic acids. Moreover, the reaction can be initiated in the absence of such other acids; i.e., it can be initiated with only the hydroxy mercaptan and hydrogen peroxide present. The mercaptans have the general formula:

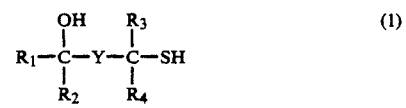

wherein $R_1$ and $R_2$ are independently selected from hydrogen, hydroxyl, halogen, and organic radicals, $R_3$ and $R_4$ are selected from hydrogen and organic radicals, and Y is an organic radical or a covalent bond between the two illustrated carbon atoms. When Y and $R_1$, $R_2$, $R_3$ or $R_4$ are organic radicals, the radicals generally have 1 to about 50 carbon atoms, preferably, 1 to about 15 carbon atoms and, most preferably, 1 to about 5 carbon atoms. The above-described organic radicals can be cyclic or acyclic, alicyclic or straight or branched chained, can contain heteroatoms such as oxygen, sulfur, nitrogen, phosphorus, etc., and can be substituted with functional groups such as thio, hydroxy, and halo substituents, etc. Preferably, the described organic radicals are saturated alkyl or cycloalkyl radicals or are aryl radicals, and all of such radicals can be substituted or unsubstituted with halogen, hydroxy, thio and/or saturated organic radicals. Preferably, any cyclic alkyl or aromatic radical contains one ring. In a more preferred embodiment, the divalent organic radical, Y, bridging the two illustrated carbon atoms, separates those two carbon atoms by about 4 atoms or less or is a covalent bond. In the most preferred embodiment of all, Y is a covalent bond, and $R_1$, $R_2$, $R_3$ and $R_4$ are all hydrogen. When the described mercaptans are reacted with hydrogen peroxide, the sulfur atom of the thio group is oxidized to a sulfonic acid group. When more than one thio group is present in the mercaptan, all thio groups can be oxidized. Preferably, however, the sulfur atom of the thio group (or groups) is selectively oxidized without oxidizing the hydroxyl group.

The process of the present invention involves, in a preferred embodiment, the production of salt-free hydroxy sulfonic acids having the formula:

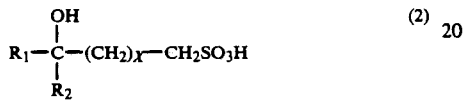

(2)

wherein $R_1$ and $R_2$ are individually selected from (1) hydrogen, (2) unsubstituted alkyl, cycloalkyl or aryl groups having 1 to about 50, preferably 1 to about 15, and most preferably 1 to about 4 carbon atoms, (3) halogen or hydroxyl substituted alkyl, cycloalkyl or aryl groups having 1 to about 50 carbon atoms, preferably 1 to about 15, and most preferably 1 to about 4 carbon atoms, (4) (halogen or hydroxyl substituted or unsubstituted) alkyl substituted cycloalkyl or aryl groups having 1 to about 50, preferably 1 to about 15, and, most preferably, 1 to about 4 carbon atoms, and (5) saturated polyhydrocarbyloxy groups preferably having 2 to about 150 carbon atoms, and X is an integer in the range of from 0 to 4; said process comprising contacting a mercaptan selected from the class consisting of hydroxy mercaptans of the formula:

(3)

wherein $R_1$, $R_2$ and X are as defined above, said contacting preferably being with a stoichiometric excess of hydrogen peroxide and said contacting resulting in the mercaptan being oxidized to form a sulfonic acid, with the hydroxyl group preferably remaining unoxidized, and most preferably with only the sulfur atom of the above formula (3) being oxidized.

In another embodiment of the invention, the process of the present invention further comprises the step of reacting a carboxylic acid with a hydroxy sulfonic acid, itself produced from the formula (1) or (3) mercaptans by reaction with hydrogen peroxide, to form a sulfo ester having the formula:

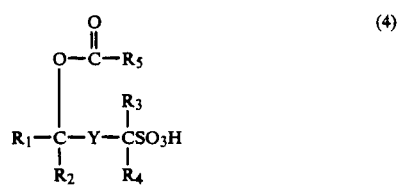

(4)

wherein $R_1$, $R_2$, $R_3$, $R_4$ and Y are as defined an organic radical as defined above for $R_1$, $R_2$, $R_3$, and $R_4$. A preferred variation of this embodiment involves the reaction of a carboxylic acid with the preferred class of hydroxy sulfonic acids (i.e., the formula (2) hydroxy sulfonic acids) to form a sulfo ester having the formula:

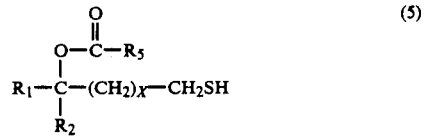

(5)

wherein $R_1 R_2 R_5$ and X are as defined above.

BRIEF DESCRIPTION OF THE DRAWING

FIG. 2 is a NMR spectrograph of a sample of isethionic acid as produced by the process of the present invention.

DETAILED DESCRIPTION OF THE INVENTION

Figure 1:
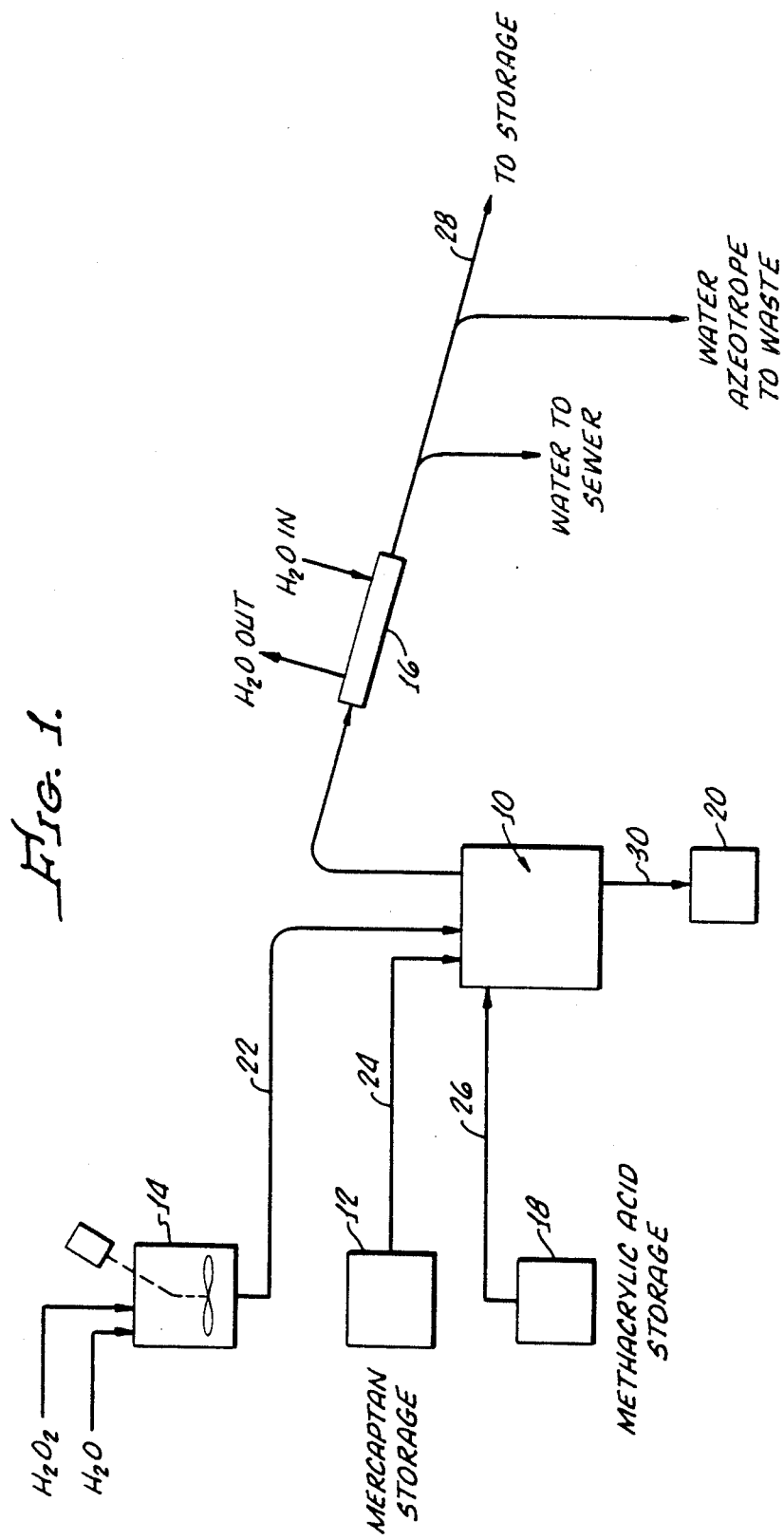
FIG. 1 is a drawing of an exemplary system for performing the process of the present invention.

According to a preferred embodiment of the present invention, the formation of hydroxy sulfonic acids is accomplished by the selective oxidation of the sulfur atom in a hydroxy-mercaptan compound having the formula:

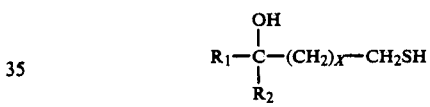

wherein $R_1$ and $R_2$ are individually selected from hydrogen, and unsubstituted alkyl, cycloalkyl or aryl groups, halogen or hydroxyl substituted alkyl, cycloalkyl or aryl groups having 1 to about 50 carbon atoms, preferably 1 to about 15 carbon atoms and, most preferably, 1 to about 4 carbon atoms and (halogen or hydroxyl substituted or unsubstituted) alkyl substituted cycloalkyl or aryl groups having 1 to about 50 carbon atoms, said cycloalkyl and aryl groups preferably having only one ring, and saturated polyhydrocarbyloxy groups preferably having 2 to about 150 carbon atoms, and X is an integer in the range of from 0 to 4. Preferably, $R_1$ and $R_2$ are selected from hydrogen and alkyl or cycloalkyl radicals, and most preferably, both $R_1$ and $R_2$ are hydrogen, and X is 0. The process comprises reacting the mercaptan with hydrogen peroxide according to the representative formula:

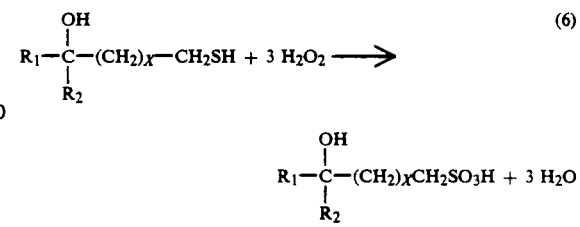

(6)

In the present invention, it is preferred that $R_1$ and $R_2$ be free of alkenyl and alkynyl unsaturation. By so doing, problems with contaminants resulting either from the reaction of double, triple or cleavable single bonds with the peroxide or the polymerization of olefins are avoided. While the saturated substituted or unsubstituted alkyl chains used either directly as $R_1$ or $R_2$ or, as a substituent on a cycloalkyl or aromatic ring, can have chain lengths of from 1 to about 50 carbon atoms, preferred, however, are chains of 1 to about 15 carbon atoms and most preferred are chains of about 4 carbon atoms or less. Examples of specific hydroxy mercaptans suitable for use as starting materials include
2-hydroxyethyl mercaptan, 1-mercapto-2-hydroxypropane,
2-mercapto-1-hydroxypropane, 1-mercapto-2-hydroxybutane,
2-mercapto-1-hydroxybutane, 2-mercapto-3-hydroxybutane,
2-mercapto-2-methyl-1-hydroxypropane,
1-mercapto-2-methyl-2-hydroxypropane,
1-mercapto-2-cyclohexyl-2-hydroxyethane,
2-mercapto-1-hydroxy-3-bromopropane,
1-mercapto-2-hydroxy-3-bromopropane,
1-mercapto-1-chloro-2-hydroxypropane,
2-mercapto-1-hydroxypropane,
2-mercapto-1-hydroxy-3-chloropropane,
1-mercapto-2-hydroxy-3-chloropropane,
2-mercapto-3-hydroxy-1-bromobutane,
2-mercapto-3-hydroxy-1-chlorobutane,
2-mercapto-1-hydroxy-3-bromobutane,
1-mercapto-2-hydroxy-3-bromobutane,
2-mercapto-1-hydroxy-3-chlorobutane,
1-mercapto-2-hydroxy-3-chlorobutane,
1-mercapto-2-methyl-2-hydroxy-3-chloropropane,
2-mercapto-3-hydroxy-1-chloropropane,
1-mercapto-2-hydroxy-2-(chloromethyl)-3-chloropropane,
2-mercapto-3-hydroxy-2-(chloromethyl)-3-chloropropane,
2-mercapto-1-methoxy-3-hydroxypropane,
1-mercapto-3-methoxy-2-hydroxypropane,
1-mercapto-2-hydroxycyclohexane,
1-mercapto-2-phenyl-2-hydroxyethane,
1-mercapto-1-phenyl-2-hydroxyethane,
1-mercapto-2-methyl-2-bromo-3-phenyl-3-hydroxypropane,
1-mercapto-3-hydroxypropane, 1-mercapto-3-hydroxybutane,
1-mercapto-4-hydroxybutane,
m-(2-hydroxyethoxy)-benzomercaptan, etc.,
and mixtures of such mercaptans.

In a broad aspect of this invention, one or more mercaptans of formula (1), supra, are reacted with hydrogen peroxide under conditions sufficient to oxidize the mercapto group to form a sulfonic acid in the presence or absence of oxidation of the hydroxyl group or other functional groups of the mercaptan reactant, and this reaction can be initiated and conducted in the absence of added acids such as sulfonic, carboxylic and percarboxylic acids. If the reaction is conducted under relatively mild oxidizing conditions, the mercapto group or groups are selectively oxidized to sulfonic acid groups without oxidation of the hydroxyl group. More severe oxidation conditions result in oxidation of other functional groups. For instance, severe oxidizing conditions result in oxidation of the hydroxyl group to form a carboxylic acid when $R_1$ and $R_2$ are hydrogen, and X is 0. The severity of oxidation is a function of reaction temperature and the concentration of hydrogen peroxide and sulfonic acid, the latter being formed during the oxidation process. Thus, oxidation severity increases as reaction temperature and the concentration of hydrogen peroxide and sulfonic acid increases. Of course, sulfonic acid concentration increases as the method progresses, unless the acid is removed during the reaction or the reaction medium is gradually diluted with solvent such as water. Generally, the mercapto group is selectively oxidized to the sulfonic acid in the absence of other oxidation reactions when the sulfonic acid concentration is maintained at a level of about 50 weight percent or less, the hydrogen peroxide concentration is maintained at about 40 weight percent or less, and reaction temperature is maintained at about 75° C. or less. Significantly higher reaction temperatures or hydrogen peroxide or sulfonic acid concentrations increase oxidation severity sufficiently to oxidize other oxidizable portions of the mercaptan reactant such as the hydroxyl group illustrated in formula (1).

In a preferred batch process embodiment of the present invention, where it is desired to prevent oxidation of the hydroxyl group illustrated in formula (1), and to oxidize only the sulfur atom therein, the oxidation reaction of Equation 1 is carried out by contacting a stream of mercaptan with an initial charge of a hydrogen peroxide solution in a reactor while a second, separate stream of peroxide is simultaneously added thereto. The initial charge provided is preferably an aqueous solution having an $H_2O_2$ concentration below about 40%, preferably between 25% and 35%, by weight. While the amount so provided can be up to 100%, it is preferably between about 20% and 40%, and, most preferably, between about 25% and 35% of the stoichiometric amount based on the amount of sulfur in the mercaptan, i.e. about 1 mole of peroxide for each mole of sulfur to be oxidized. When the upper limit of $H_2O_2$ concentration is held below 40%, it is found that the sulfur atom in the mercapto (—SH) group is selectively oxidized while the hydroxyl (—OH) group remains essentially intact. Concentrations lower than 20% can be used for the initial peroxide charge, but it has been found that the energy required to subsequently remove excessive amounts of water during and after the reaction increases rapidly, thus imposing a serious cost penalty when concentrated acid solutions, such as those used in sulfo ester production, are produced (see Examples 1 and 2 hereinbelow). Once the reaction has started, the second stream of peroxide added need not be held to the 40% concentration limitation, and concentrations of 50% and even higher may safely be used since the 3 moles of water generated by the oxidation of each mole of sulfur, along with the peroxide-depleted water in the reactor will act to keep the effective level of peroxide concentration below 40% at all times. By so doing, subsequent problems with removing excess water are minimized. Product costs and purification problems are minimized by keeping the total amount of peroxide provided below a 10% excess of the stoichiometric amount (based on the total sulfur content involved in the oxidation step of the process), preferably, below a 5% excess and, most preferably, below a 1% excess. Of course, excess water can be removed, if desired, either during the reaction or after the reaction has been completed by any suitable means such as boiling, vacuum distillation, solvent extraction, etc.

Because of the highly exothermic nature of the oxidation step, particular care must be taken to keep the overall temperature of the reaction mass as low as possible; preferably, below about 75° C. Depending on the purity of the individual reactants, it is sometimes necessary to heat the initial charge of peroxide solution somewhat to start the oxidation reaction. However, the highly exothermic reaction, once started, will be self sustaining without the further external addition of heat. It has been found that the amount of preheating necessary can be considerably reduced, or even avoided entirely, by adding between about 0.5 to 4, and, preferably, 1 to 3 ppm of a mild reducing agent to the initial peroxide charge. The particular agent used is not critical and compounds such as sodium bisulfite, ferrous sulfate, ferrous chloride, cuprous chloride and the like are suitable, with ferrous sulfate hydrate ($FeSO_4 \cdot 7H_2O$) being preferred. When added at the very low levels described above, the particular salt used has essentially no effect on final product purity.

The oxidation of the mercaptan to form the sulfonic acid can be conducted in relatively dilute reaction media, e.g., 70 weight percent water or more, in which case control of reaction temperature due to the oxidation exotherm is generally not problematical and does not require removal of substantial reaction heat. However, in the preferred embodiment of this invention, it is desired to produce a relatively concentrated sulfonic acid reaction product in which event the reaction is conducted in more concentrated media and temperature control by heat removal becomes essential when it is desired to prevent oxidation of other portions of the mercaptan reactant such as the hydroxyl group. To avoid problems with the aforementioned explosive acceleration of reaction velocity which can occur in concentrated reaction media, excess heat is removed from the reaction vessel as quickly as possible. In a preferred embodiment, this is accomplished by adjusting the flow of the mercaptan into the reactor to a rate sufficient to keep the reaction going, but insufficient to cause the generation of excessively large amounts of heat. Keeping the temperature low is further aided by conducting the reaction under a vacuum sufficient to lower the boiling point of water to below about 75° C., preferably between about 60 and 70° C. At such a temperature, the peroxide is stable and does not decompose. In the preferred process, such excess heat is easily and quickly removed simply by evaporating and subsequently condensing out at least a portion of the water in the reactor. While those of skill in the art will recognize that other means such as jacketed reactors, chilling coils and the like may be used to control the temperature within the reactor, water evaporation carries off the largest amount of heat and further offers the advantages of providing both a more concentrated solution for the final reaction product and a more direct means for controlling the rate of oxidation than might otherwise be possible.

An important feature of one preferred embodiment of the present invention is the adjustment of the flow rate of the peroxide streams, after initial start-up, to assure that at all times there is a stoichiometric excess of peroxide present. In one procedure for accomplishing this objective, a peroxide flow rate is established which ensures that the total amount of peroxide will be provided to the reactor prior to the last mercaptan addition. To obtain maximum process control, once the last of the peroxide is added to the reactor, its concentration is then carefully monitored. By so doing, it becomes possible to stop the mercaptan addition very close to the point where the peroxide is completely exhausted. In small batch sizes, such as might be produced in the laboratory, this is signalled by a significant reduction in the amount of heat generated, i.e., the reaction medium stops boiling. In larger batch sizes, instrumental and colorometric techniques are available for peroxide level monitoring. With careful process control, stopping the mercaptan addition within 100 ppm of peroxide exhaustion has not proven to be particularly difficult. In addition, when the reaction is carried out as described, yields above 80%, most often above 90% and, with proper process control, very often approaching 100% of theoretical can be achieved.

When the reaction involved in the preferred, selective oxidation embodiment of this invention is completed, the product contained in the reaction vessel is relatively concentrated, e.g. about 40 weight percent as an aqueous solution of the hydroxy sulfonic acid of relatively high purity, e.g. 99 percent plus purity can be achieved. This solution can be concentrated by boiling at reduced pressure after thermally decomposing residual peroxide at, e.g. 190° to 200° F. As is shown in Example 2 below, the concentrated solution so provided can be used directly in reactions with carboxylic acids to produce a class of materials identified generically as sulfo esters according to the representative reaction:

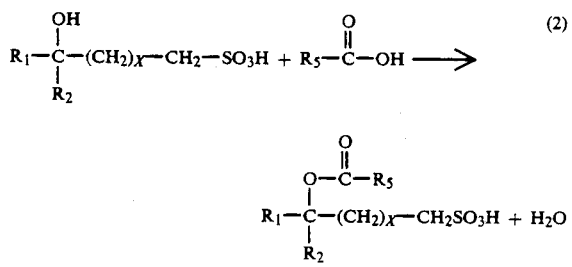

wherein $R_1$, $R_2$, X and $R_5$ are as hereinabove defined.

One group of such esters of particular interest is the reaction product of hydroxy sulfonic acids with olefinically unsaturated carboxylic acids having from 3 to about 50 carbon atoms. Of particular interest are alpha-beta ethylenically unsaturated carboxylic acids which react to form polymerizable surfactants and stabilizers which find wide use in the production of many polymers, such as polyvinylidene chloride (PVDC) copolymers. For such applications, suitable carboxylic acids include acrylic acid, methacrylic acid, ethylacrylic acid, propylacrylic acid, butylacrylic acid, pentylacrylic acid, hexylacrylic acid, cyclohexylacrylic acid, chloroacrylic acid, phenylacrylic acid and furylacrylic acid and mixtures thereof with methacrylic acid being preferred. Other acids which may be used include: 2-butenoic acid, 2-ethylhexyl-2-butenoic acid, 2-pentenoic acid, 3-methyl-3-pentenoic acid, 2-heptenoic acid, 4-ethyl-2-heptenoic acid, etc. In the United States, copolymers produced with sulfoethylmethacrylate (SEM), the sulfo esterification reaction product of isethionic acid (2-hydroxy ethyl sulfonic acid) and methacrylic acid (MAA), are used in the production of various packaging films which have been approved by the U.S. Food and Drug Administration for food and drug distribution.

To produce such a material, the concentrated acid product as produced by the present invention can be directly reacted with MAA (as shown in Example 2 below). To drive the esterification reaction to completion, between 1 and 10, and preferably between 3 and 6, moles of MAA are used and some of the water generated within the reactor is distilled off as a water/MAA azeotrope. To prevent the MAA from self polymerizing, small quantities of one or more polymerization inhibitors are also added with the mixture being reacted under a vacuum of from about 20 mm. Hg. to about 200 mm. Hg. and a temperature of from about 50° C. to about 150° C. to produce SEM, using esterification procedures described by Sheetz et al. in U.S. Pat. No. 3,359,305 (herein incorporated by reference). At the conclusion of the reaction, any residual water in the reactor is removed by continued azeotropic distillation. Once the water is all removed, any remaining MAA is distilled off under vacuum and recovered for reuse. The water/MAA-free SEM product of this reaction is of sufficient purity that it can be incorporated directly into many emulsion polymerization reactions.

As with any system in which unstable and corrosive materials are used, careful attention should be paid to the design and materials of construction used for the peroxide handling facilities and the reactor itself. In regard to the peroxide solutions, the facility should be kept clean and free of contaminants which might cause spontaneous peroxide decomposition. Furthermore, since most hydroxy sulfonic acids are strong acids and readily attack carbon steel and similar materials of construction, a glass lined reactor is preferred. However, it is recognized that other materials of construction which are resistant to strong sulfuric acid solutions may be used with equal facility. Materials of construction meeting these criteria are well known in the art. Failure to use such materials has been found to result in a finished product having levels of iron or other contaminants sufficient to make the final product unacceptable for many applications.

FIG. 1 shows an exemplary batch reactor system which can be used to produce SEM and similar materials according to the present invention. As shown therein, the system comprises reactor 10, and associated mercaptan storage tank 12, peroxide mixing tank 14, condenser 16, methacrylic acid storage tank 18 and product storage 20. Connecting these units to reactor 10 are conventional piping, vacuum and hydraulic pumps, control and heating/cooling systems and the like. Aside from the caveats recited above, there are no special requirements for any of this equipment. In the preferred embodiment, both the 2-hydroxyethyl mercaptan and methacrylic acid used can be commercially supplied bulk materials and stored for use in storage tanks 12 and 18. Similarly, hydrogen peroxide, can be purchased in solution concentrations of 50% by weight or even higher, and, for the initial charge material, simply diluted in mixing tank 14 with distilled or deionized water to a concentration of between 25% and 35% by weight before being pumped into reactor 10 through pipeline 22. There, the diluted solution is heated (if necessary) to an initial starting temperature of about 60° C. (using an internal heater such as a steam coil, not shown) at a vacuum of about 160 mm. Hg. Additional undiluted peroxide and the mercaptan are then controllably admitted through pipelines 22 and 24, respectively. Once the oxidation reaction has started, temperature control is achieved by allowing at least a portion of the water in the reactor to evaporate into condenser 16, the vacuum level and, therefore, the rate of evaporation being adjusted to allow sufficient heat to be removed to keep the temperature of the reactive medium below about 75° C.

At the completion of the reaction, the vacuum is broken, and excess water and peroxide boiled off to produce a peroxide-free concentrated solution.

Where the product of this invention is used as a starting material for SEM and similar sulfo esters, methacrylic acid from storage tank 18 is then added to reactor 10 via pipeline 26 and reacted as hereinabove described. During the reaction, a water/MAA azeotrope is distilled off to drive the reaction to conclusion. At the conclusion of the reaction, any remaining water and MAA are distilled off under vacuum. After the water is removed (as shown by a significant rise in the boiling point), the remaining MAA is removed by vacuum distillation and returned via pipeline 28, to storage tank 18 for reuse. At the conclusion of this distillation, the SEM product is removed through pipeline 30 to storage facility 20 where it is drummed or otherwise made available for subsequent use.

EXAMPLES

Example 1

A 50 gallon, glass-lined reactor fitted with an overhead condenser and separate $H_2O_2$ and 2-hydroxyethyl mercaptan (2HEM) inlet lines is charged, at a vacuum of 142 mm. (2.7 psia), with a mixture comprising 18.7 Kg. (41.2 lbs.) 33% $H_2O_2$ and 0.079 g. of solid $FeSO_4 \cdot H_2O$. This is heated to a temperature of 66° C. (150° F.). Once this temperature is reached, 17.25 Kg. (38 lbs.) of 2HEM and 33.2 Kg. (73.2 lbs.) of 50% $H_2O_2$ are added at the rates of 0.72 Kg. (1.58 lbs.)/15 minutes and 1.7 Kg. (3.76 lbs.)/15 minutes, respectively, over a six-hour period, said temperature of about 66° C. being maintained throughout. The addition rates are such that the $H_2O_2$ can be completely added about 1 hour before the final 2HEM increment is added. After the last $H_2O_2$ addition, the peroxide level is closely monitored, using colorometric analysis, to avoid overshooting the endpoint of the reaction (i.e., exhaustion of the $H_2O_2$). The end of the reaction is also indicated by cessation of boiling in the reaction mixture. At this point, the mixture comprises an essentially peroxide-free solution of isethionic acid (ITA) having an aqueous concentration of about 40%. This is first heated at a temperature of about 195° F. for about four hours to decompose the residual peroxide and then concentrated by boiling the solution at a temperature of about 160° F., under vacuum, until an essentially saturated ITA concentration of about 85% is reached. Analysis of this solution shows the isethionic acid produced by this process to have a purity in excess of 99%. The yield is essentially 100% of theoretical. FIG. 2 is an NMR spectrograph of this product dissolved in $D_2O$. Starting from the left side, it shows as peak (a), DHO; as peak (b), methylene protons adjacent to the —OH, and as peak (c), methylene protons adjacent to the —$SO_3H$ peak. No peaks representative of other structures appear. Such a spectrograph is essentially identical to that shown by commercial standards for this compound.

Example 2

To the reactor containing the concentrated isethionic acid solution of Example 1 is added 95.2 Kg. (209.5 lbs.) of MAA to achieve a MAA/ITA molar ratio of about 5:1 along with 14 grams of N,N' diphenyl-p-phenylene diamine and 140 grams of monomethyl ether hydroquinone, both serving as polymerization inhibitors. The mixture is heated for about 6 hours under a vacuum of about 90 mm. Hg. at a temperature of about 80° C. to form sulfoethyl methacrylate according to the reaction:

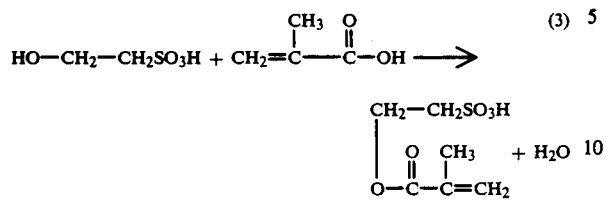

with water of reaction and residual water from the oxidation reaction being continuously removed by azeotropic distillation of a water/MAA mixture under vacuum. At the completion of the reaction, as shown by the cessation of the azeotropic distillation and an increase in the pot temperature, any remaining MAA is removed by vacuum distillation at a pressure of about 10 mm. Hg. The resultant product is sulfoethyl methacrylate having a purity of about 90-95% with methacrylic acid as the major impurity.

It should be understood that although the process is exemplified as a batch reaction, continuous processing is also possible with proper process equipment and controls and is to be considered within the scope of the present invention.

ADVANTAGES OF THE INVENTION

The present invention is a process which results in the high yield production aqueous solutions of essentially pure salt-free hydroxy sulfonic acids in general and isethionic acid in particular in a reaction which does not require the presence of additional sulfonic acid as a diluent. In a preferred embodiment the process achieves concentrated solutions of these acids at a level of purity sufficient to allow their direct use in esterification reactions to produce sulfo esters, said esters being widely used as stabilizers in many emulsion copolymerization reactions. Further, the process of the present invention, as exemplified in Example 1, is adaptable to simple process control systems to accomplish such results at significantly lower costs than processes taught in the prior art.

This invention may be embodied in other specific forms without departing from the spirit or essential characteristics thereof. The present embodiments and examples are, therefore, to be considered in all respects as illustrative and not restrictive, the scope of the invention being indicated by the appended claims, and all changes which come within the scope and equivalency of the claims are, therefore, intended to be embraced therein.

I claim:

1. A process for producing a hydroxy sulfonic acid by the oxidation of a mercaptan selected from the class consisting of hydroxy mercaptans of the formula:

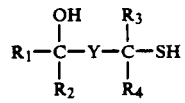

wherein $R_1$ and $R_2$ are independently selected from hydrogen, halogen, hydroxy and unsubstituted or substituted cyclic, acyclic, alicyclic, straight or branched chain organic groups, $R_3$ and $R_4$ are independently selected from hydrogen and organic groups as defined for $R_1$ and $R_2$, and Y is a covalent bond or an organic group as defined for $R_1$ and $R_2$, said process comprising the steps of:

(a) adding a reactor an aqueous hydrogen peroxide solution having a concentration below about 40% by weight in an amount equal to between about 20% and about 40% of the stoichiometric ratio based on the total quantity of mercaptan being oxidized, said solution being heated to a temperature below about 75° C.;

(b) adding said mercaptan to said reactor; and (c) simultaneously adding an additional stream of aqueous hydrogen peroxide into the reactor, the amount of hydrogen peroxide so added, when combined with the hydrogen peroxide previously introduced into the reactor, being an excess of no more than about 10% greater than the stoichiometric amount required to selectively oxidize the mercaptan to a sulfonic acid, the relative rates of said additions being adjusted so that the addition of the hydrogen peroxide is complete before the final addition of the mercaptan is made, with the temperature of the reacting medium being maintained below about 75° C.

2. The process of claim 1 wherein said mercaptan is selected from the group consisting of 2-hydroxyethyl mercaptan, 1-mercapto-2-hydroxypropane, 2-mercapto-1-hydroxypropane, 1-mercapto-2-hydroxybutane, 2-mercapto-1-hydroxybutane, 2-mercapto-3-hydroxybutane, 2-mercapto-2-methyl-1-hydroxypropane, 1-mercapto-2-methyl-2-hydropropane, 1-mercapto-2-cyclohexyl-2-hydroxyethane, 2-mercapto-1-hydroxy-3-bromopropane, 1-mercapto-2-hydroxy-3-bromopropane, 1-mercapto-1-chloro-2-hydroxypropane, 2-mercapto-1-hydroxypropane, 2-mercapto-1-hydroxypropane, 2-mercapto-1-hydroxy-3-chloropropane, 1-mercapto-2-hydroxy-3-chloropropane, 2-mercapto-3-hydroxy-1-bromotuane, 2-mercapto-3-hydroxy-1-chlorobutane, 2-mercapto-1-hydroxy-3-bromobutane, 1-mercapto-2-hydroxy-3-bromobutane, 2-mercapto-1-hydroxy-3-chlorobutane, 1-mercapto-2-hydroxy-3-chlorobutane, 1-mercapto-2-methyl-2-hydroxy-3-chloropropane, 2-mercapto-3-hydroxy-1-chloropropane, 1-mercapto-2-hydroxy-2-(chloromethyl)-3-chloropropane, 2-mercapto-3-hydroxy-2-(chloromethyl)-3-chloropropane, 2-mercapto-1-methoxy-3-hydroxypropane, 1-mercapto-3-methoxy-2-hydroxypropane, 1-mercapto-2-hydroxycyclohexane, 1-mercapto-2-phenyl-2-hydroxyethane, 1-mercapto-1-phenyl-2-hydroxyethane, 1-mercapto-2-methyl-2-bromo-3-phenyl-3-hydroxypropane, 1-mercapto-4-hydroxybutane, and mixtures thereof.

3. A process for production of hydroxy sulfonic acids by the oxidation of a mercaptan selected from the class consisting of hydroxy mercaptans of the formula:

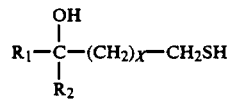

wherein $R_1$ and $R_2$ are individually selected from hydrogen, and unsubstituted alkyl, cycloalkyl or aryl groups of 1 to 50 carbon atoms, halogen or hydroxyl substituted alkyl, cycloalkyl or aryl groups having 1 to about 50 carbon atoms, (halogen or hydroxyl substituted or unsubstituted) alkyl substituted cycloalkyl or aryl groups having 1 to about 50 carbon atoms, and saturated polyhydrocarbyloxy groups, and X is an integer in the range of from 0 to 4, said process comprising the steps of:

(a) adding to a reactor an amount of an aqueous hydrogen peroxide solution having a concentration below about 40% by weight in an amount equal to between about 20% and about 40% of the stoichiometric ratio based on the total quantity of mercaptan being oxidized, said solution being heated to a temperature below about 75° C.;

(b) adding an amount of said mercaptan; and (c) simultaneously adding an additional stream of aqueous hydrogen peroxide into the reactor, the amount of peroxide so added, when combined with the hydrogen peroxide previously introduced into the reactor, being an excess of hydrogen peroxide equal to no more than about 10% above the stoichiometric amount necessary to selectively oxidize the mercaptan to a sulfonic acid, the relative rates of said additions being adjusted so that the addition of the peroxide is complete before the final addition of the mercaptan is made, with the temperature of the reacting medium being maintained below about 75° C.

4. The process of claim 3 wherein $R_1$ and $R_2$ each has between 1 and about 30 carbon atoms.

5. The process of claim 3 wherein the hydrogen peroxide concentration is between 25% and 35% by weight.

6. The process of claim 3 wherein the total amount of hydrogen peroxide provided is no more than 5% above stoichiometric.

7. The process of claim 6 wherein the total amount of hydrogen peroxide provided is no more than 1% above stoichiometric.

8. The process of claim 3 wherein said oxidation of said mercaptan is initiated in the absence of added acid.

9. The process of claim 3 further comprising the addition of between 0.5 ppm and 4 ppm of a mild reducing agent.

10. The process of claim 9 wherein the concentration of said reducing agent is between 1 ppm and 3 ppm.

11. The process of claim 1 wherein said reducing agent comprises $FeSO_4]H_2O$.

12. The process of claim 3 further comprising the step of concentrating the hydroxy sulfonic acid solution.

13. The process of claim 12 wherein said concentration step comprises evaporating a sufficient amount of the water of dilution of the hydrogen peroxide solution and the water formed by the reduction of the hydrogen peroxide to create an essentially saturated solution of hydroxy sulfonic acid.

14. The process of claim 3 wherein said mercaptan is 2-hydroxy ethyl mercaptan.

15. The process of calim 3 wherein all R groups, if organic, contain no more than about 15 carbon atoms.

16. The process of calim 3 wherein all R groups, if organic, contain no more than about 10 carbon atoms.

17. The process of calim 3 wherein all R groups, if organic, contain no more than about 4 carbon atoms.

18. A process for the production of isethionic acid from 2-hydroxyethyl mercaptan comprising the steps of:

(a) adding to an enclosed reactor an amount of a 25% to 35% by weight aqueous solution of hydrogen peroxide, said amount being equal to between about 25% and about 35% of the stoichiometric amount to selectively oxidize the hydrosulfide group of the total amount of said mercaptan to a sulfonic acid group;

(b) heating said solution under a vacuum sufficient to lower the boiling point of water to about 75° C. or less; and (c) adding to said reactor an amount of said mercaptan while simultaneously adding to the reactor, an additional stream of aqueous hydrogen peroxide at a rate such that the quantity of peroxide within the reactor is always at a concentration greater than the stoichiometric amount for the amount of mercaptan therein, the total amount of peroxide added in steps (a) and (c) being an excess of no more than 5% greater than the stoichiometric amount required to selectively oxidize the total amount of sulfur in the mercaptan while leaving the hydroxyl group intact, the rates of such additions further being adjusted so that the temperature of the reactants is maintained below about 75° C.

19. The process of claim 18 further comprising controllably evaporating at least a portion of the water of dilution of the hydrogen peroxide and the water generated by the oxidation of the thiol group of said mercaptan.

20. A process for the production of isethionic acid from 2-hydroxy ethyl mercaptan comprising the steps of:

(a) adding to an enclosed reactor a mixture comprising an amount of a 30% to 35% aqueous solution of hydrogen peroxide equal to between about 25% to 30% of the stoichiometric amount to selectively oxidize the thiol group of said mercaptan to a sulfonic acid group and between 1 ppm and 3 ppm of a mild reducing agent;

(b) heating the mixture in said reactor under a vacuum sufficient to lower the boiling point of water to below about 70° C.; and then (c) adding an amount of said mercaptan while simultaneously adding an additional stream of aqueous hydrogen peroxide, the rates of such additions being adjusted such that the quantity of peroxide within the reactor is always at a concentration greater than the stoichiometric amount for the amount of mercaptan therein and the total amount of peroxide provided being an excess of no more than 1% greater than the stoichiometric amount required for the total amount of sulfur in the mercaptan added, the rates of such additions further being adjusted so that the temperature of the reactants is maintained between about 65° C. and 75° C.

21. The process of claim 20 wherein said mild reducing agent comprises $FeSO_4 \cdot 7H_2O$.

22. The process of claim 20 further comprising controllably evaporating at least a portion of the water of dilution of the hydrogen peroxide and the water generated by the oxidation of the thiol group.

* * * * *

UNITED STATES PATENT AND TRADEMARK OFFICE
CERTIFICATE OF CORRECTION

PATENT NO. : 4,987,250

DATED : January 22, 1991

INVENTOR(S) : Dennis E. McGee and Ted S. Hallen

It is certified that error appears in the above-identified patent and that said Letters Patent is hereby corrected as shown below:

Column 13, line 47, claim 11, line 1, delete "1" and insert therefor -- 9 --.

Column 13, line 48, claim 11, line 2 delete "$FeSO_4]H_2O$" and insert therefor -- $FeSO_4 \cdot 7H_2O$ --.

Signed and Sealed this

Thirtieth Day of June, 1992

Attest:

DOUGLAS B. COMER

Attesting Officer

Acting Commissioner of Patents and Trademarks